(12) United States Patent
Grespan et al.

(10) Patent No.: US 9,302,457 B2
(45) Date of Patent: Apr. 5, 2016

(54) LIQUID OPTICALLY CLEAR ADHESIVE LAMINATION PROCESS CONTROL

(71) Applicant: Apple Inc., Cupertino, CA (US)

(72) Inventors: Silvio Grespan, Cupertino, CA (US); Shih-Min Hsu, Tainan (TW); Heng-Hsi Wu, Kaohsiung (TW); Kuo-Hua Sung, San Jose, CA (US); Cyrus Y. Liu, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 287 days.

(21) Appl. No.: 13/766,393

(22) Filed: Feb. 13, 2013

(65) Prior Publication Data
US 2014/0071417 A1    Mar. 13, 2014

Related U.S. Application Data

(60) Provisional application No. 61/698,565, filed on Sep. 7, 2012.

(51) Int. Cl.
*B32B 38/00* (2006.01)
*G01N 33/00* (2006.01)
*G01B 11/14* (2006.01)
*G03F 7/20* (2006.01)
*G06F 3/041* (2006.01)

(52) U.S. Cl.
CPC ............ *B32B 38/0008* (2013.01); *G01B 11/14* (2013.01); *G01N 33/00* (2013.01); *G03F 7/70008* (2013.01); *G06F 3/0412* (2013.01); *G06F 2203/04103* (2013.01)

(58) Field of Classification Search
CPC ...... B32B 3/0008; G01N 33/00; G01B 11/14; G03F 7/70008; G06F 3/0412
USPC ........................................... 156/272.2, 275.5
See application file for complete search history.

(56) References Cited

U.S. PATENT DOCUMENTS 3,826,014 A    7/1974    Helding
4,988,424 A    1/1991    Woodward et al.
(Continued)

FOREIGN PATENT DOCUMENTS

JP          11133442 A  *  5/1999
KR       101998080065        11/1998
(Continued)

OTHER PUBLICATIONS

Taiwanese Patent Application No. 102132267—Office Action dated Dec. 8, 2014.
(Continued)

*Primary Examiner* — Daniel McNally
(74) *Attorney, Agent, or Firm* — Downey Brand LLP

(57) ABSTRACT

Methods and devices for using liquid optically clear adhesives (LOCAs) are described. A method for detecting uncured LOCA between a first substrate and a second substrate is described. In addition, an improved method for curing a laminated stack up having LOCA between a first substrate and a second substrate is described. The method includes a pre-curing method involving variable exposure of the LOCA. In addition, an improved light emitting diode (LED) unit assembly for exposing a laminated stack up to ultraviolet (UV) light during a pre-curing process is described. A method for testing the LED unit assembly prior to a pre-curing process is described.

19 Claims, 15 Drawing Sheets

(56) References Cited

U.S. PATENT DOCUMENTS

| | | | |
|---|---|---|---|
| 5,062,877 A * | 11/1991 | Borrelli et al. | 65/30.13 |
| 5,725,972 A | 3/1998 | Takeshita | |
| 6,004,413 A * | 12/1999 | Couttenier | 156/99 |
| 6,313,894 B1 | 11/2001 | Sekine et al. | |
| 8,222,811 B2 | 7/2012 | Vaufrey et al. | |
| 2003/0017310 A1 | 1/2003 | Young | |
| 2004/0094727 A1 | 5/2004 | Holmes | |
| 2004/0149380 A1 | 8/2004 | Miyamoto et al. | |
| 2006/0164961 A1* | 7/2006 | Vromas | 369/275.1 |
| 2008/0023639 A1* | 1/2008 | Kawasaki et al. | 250/372 |
| 2008/0230177 A1 | 9/2008 | Crouser et al. | |
| 2010/0277684 A1 | 11/2010 | Fukushima et al. | |
| 2012/0026102 A1* | 2/2012 | Chang et al. | 345/173 |

FOREIGN PATENT DOCUMENTS

| | | |
|---|---|---|
| WO | WO2011112447 A2 | 9/2011 |
| WO | WO2012024217 A1 | 2/2012 |
| WO | WO2012082706 A2 | 6/2012 |
| WO | WO2012087804 | 6/2012 |
| WO | WO2012138495 A1 | 10/2012 |

OTHER PUBLICATIONS

Korean Patent Application No. 10-2013-107144—Office Action dated Feb. 2, 2015.

\* cited by examiner

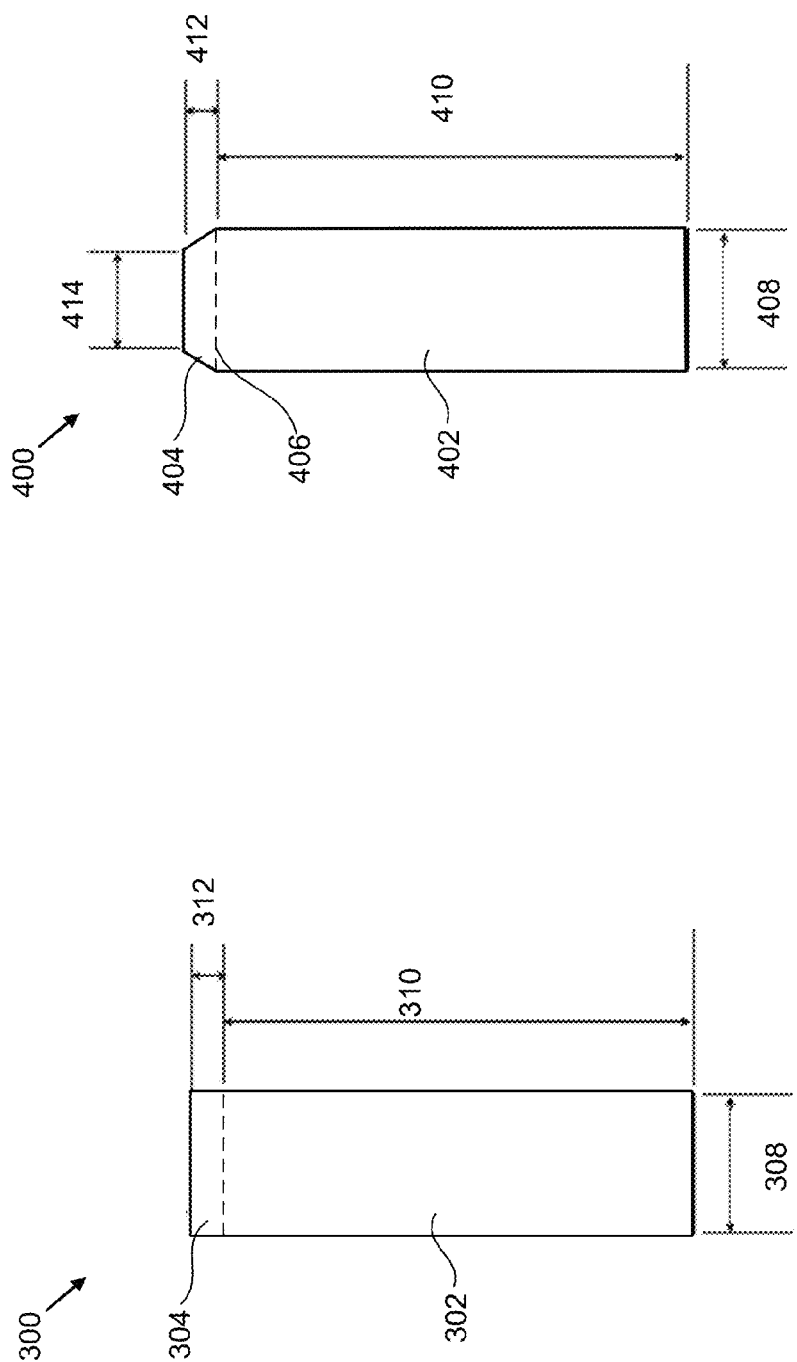

LIQUID OPTICALLY CLEAR ADHESIVE LAMINATION PROCESS CONTROL

FIELD OF THE DESCRIBED EMBODIMENTS

The described embodiments relate generally to liquid adhesives used to bond substrates. More particularly, improved methods for curing liquid optically clear adhesive (LOCA) between substrates are described.

BACKGROUND

Display and touch screens can include multiple substrates stacked in sequence, including items such as a liquid crystal display, one or more filters to modify the light to and from the liquid crystal display and a cover glass or lens to provide protection to display components and provide a user with a finished surface. In many cases one or more of these substrates are bonded together using liquid optically clear adhesives (LOCAs). The use of LOCA has become popular in the manufacture of the current generation of display applications in part because, compared to adhesive tape, LOCA is easier to rework and has good gap filling capability.

Since LOCAs are in liquid form, they can require special care when applying them to substrates. In particular, care should be taken to ensure that the introduction of bubbles or voids between the substrates is avoided. In addition, care should be taken to avoid inconsistent curing of the LOCA in different locations of the substrates so as to prevent distortions and visible defects. Consistent process parameters related to LOCA applications can be difficult to control in a manufacturing setting. Inconsistent process parameters can lead to high part rejection rates or defects in the visual quality of the final product.

SUMMARY

This paper describes various embodiments that relate liquid optically clear adhesives (LOCAs). Methods for applying and curing LOCAs between two or more substrates are described.

According to one embodiment described herein, a method for detecting uncured LOCA between a first substrate and a second substrate is described. The method can include: defining at least one potential region of uncured LOCA between the first and second substrates; determining an edge location of the first substrate for inserting a probe between the first and second substrates in a region proximate to the at least one potential region of uncured LOCA; inserting a probe end of the probe between the first and second substrates at the edge location of the first substrate, wherein the probe end has a depth line used to determine the depth of insertion of the probe; and extracting the probe and inspecting the probe end to determine the presence of uncured LOCA.

According to another embodiment, a method for curing a laminated stack up including a LOCA between a first substrate and a second substrate is described. The laminated stack up can include a pre-curing area and a curing area which includes the pre-curing area. The method can include: pre-curing the pre-curing area of the laminated stack up, the pre-curing area including a first laminated stack-up portion and a second laminated stack-up portion, the pre-curing process involving: exposing the first laminated stack up portion to a first amount of ultraviolet (UV) light, wherein a first LOCA portion corresponding to the first laminated stack up portion becomes at least partially cured; and exposing the second laminated stack up portion adjacent to the first laminated stack up portion to a second amount of UV light, wherein a second LOCA portion corresponding to the second laminated stack up portion becomes at least partially cured. Once the pre-curing process is complete, the method can include exposing the curing area of the laminated stack up to a third amount of UV light, where a remaining LOCA portion that does not include the first and second LOCA portions becomes at least partially cured. As a result, the transitions from the first, second and remaining LOCA portions can be substantially non-visible.

According to another embodiment, a light emitting diode (LED) unit assembly for exposing a laminated stack up to UV light during a pre-curing process is described. The laminated stack up includes a LOCA between a first substrate and a second substrate. The LED unit assembly can include: a mask having an opaque portion and a transparent portion and an LED unit comprising a number of UV light emitting LEDs. The opaque portion of the mask can be configured to block UV light from passing through and the transparent portion of the mask can be configured to allow UV light to pass through. The transparent portion can have a shape and size corresponding to a pre-curing area of the laminated stack up. The LEDs can be arranged in an array that has a shape and size corresponding to the shape and size of the transparent portion of the mask. During a pre-curing process, the array is aligned with the transparent portion such that UV light shining through the transparent portion is substantially perpendicular to the mask and substantially no stray UV light impinges on the laminated stack up. As a result, there are substantially no visible defects in the LOCA.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

FIGS. 3 and 4 show different embodiments of probes used to detect uncured LOCA between substrates.

DETAILED DESCRIPTION OF SELECTED EMBODIMENTS

Representative applications of methods and apparatus according to the present application are described in this section. These examples are being provided solely to add context and aid in the understanding of the described embodiments. It will thus be apparent to one skilled in the art that the described embodiments may be practiced without some or all of these specific details. In other instances, well known process steps have not been described in detail in order to avoid unnecessarily obscuring the described embodiments. Other applications are possible, such that the following examples should not be taken as limiting.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting. That is, other embodiments may be used, and changes may be made without departing from the spirit and scope of the described embodiments.

Described herein are methods for improving process controls in the application of liquid optically clear adhesives (LOCAs) used in manufacturing product lines. LOCAs are generally used in displays and touch panel applications to bind various substrates to each other, such as cover glasses/lenses to sensor units. The use of LOCAs can improve the optical characteristics of the devices as well as improve other attributes such as durability when compared to the use of traditional adhesives such as adhesive tapes. Some advantages of LOCA, when compared to traditional adhesives, are its re-workable property and ability to bind to non-even surfaces, while continuing to add transparent optical properties and durability to the device.

Figure 1:
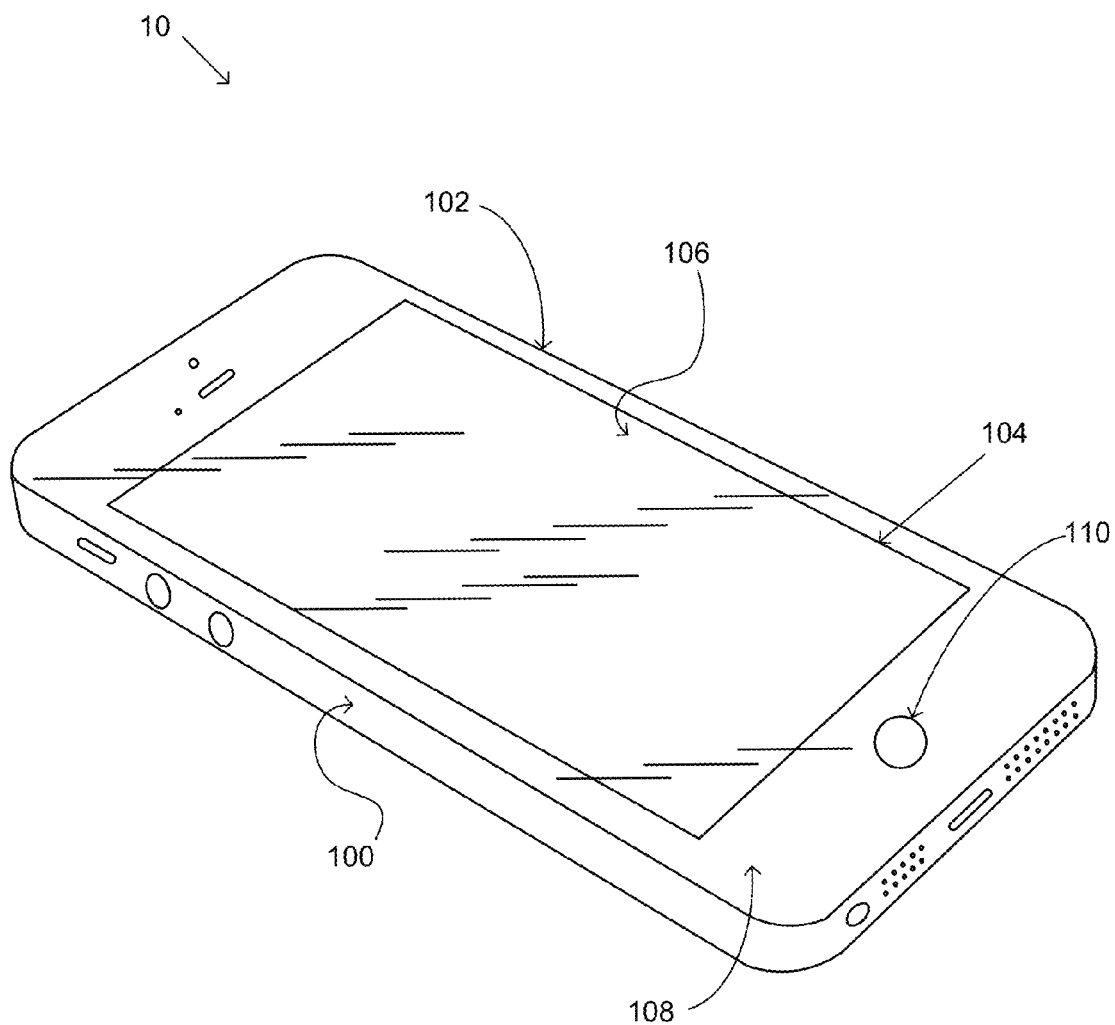
FIG. 1 shows a perspective view of a portable electronic device having a touch panel screen.

Methods described are well suited for manufacture of displays and touch panel screens as part of computing devices including desktop computers, laptop computers, smart phones and media players, such as those designed and sold by Apple Inc. headquartered in Cupertino, Calif. FIG. 1 shows a perspective view of a fully assembled portable electronic device 10 in accordance with an embodiment described herein. Portable electronic device 10 can be sized for one-handed operation and placement into small areas such as a pocket, i.e., portable electronic device 10 can be a handheld pocket sized electronic device. By way of example, the portable electronic device 10 may correspond to a computer, media device, telecommunication device and/or the like. The portable electronic device 10 can generally correspond to a smart phone, music player, game player, video player, personal digital assistant (PDA), and/or the like.

Portable electronic device 10 includes a housing 100 configured to at least partially enclose any suitable number of components associated with portable electronic device 10. For example, housing 100 may enclose and support internally various electrical components (including integrated circuit chips and other circuitry) to provide computing operations for the device. In one embodiment, housing 100 is integrally formed in such a way as to constitute a single complete unit. Housing 100 can be formed of any number of materials including for example plastics, metals, ceramics and the like.

Portable electronic device 10 also includes a cover glass 106 that has a planar outer surface. The outer surface can for example be flush with an edge 102 of the housing wall that surrounds the edge of the cover. Cover glass 106 cooperates with the housing 100 to enclose the portable electronic device 10. Although the cover glass 106 can be situated in a variety of ways relative to housing 100, in the illustrated embodiment, cover glass 106 is disposed within and proximate the mouth of the cavity of the housing 100. That is, the cover 106 fits into an opening 108. In one embodiment, cover glass 106 is a protective top layer of transparent or semitransparent material (clear) such that a display screen 104 is visible therethrough. That is, the cover glass 106 can serve as a window for the display screen 104 (i.e., the transparent cover overlays the display screen). Display screen 104 can be used to display a graphical user interface (GUI) as well as other information to the user (e.g., text, objects, graphics). Display screen 104 can be part of a display unit (not shown) that is assembled and contained within the housing 100. In one particular embodiment, the cover is formed from glass (e.g., cover glass), and more particularly highly polished glass. It should be appreciated, however, that other transparent materials such as clear plastic may be used. Cover glass 106 can include a hole to accommodate a user clickable input button 110 (home button) that can be used to provide a user input event to the portable electronic device 10.

In one embodiment, the viewing region may be touch sensitive for receiving one or more touch inputs that help control various aspects of what is being displayed on the display screen. In some cases, the one or more inputs can be simultaneously received (e.g., multi-touch). In these embodiments, one or more touch sensing layers (not shown) can be located below cover glass 106. A touch sensing layer can for example be disposed between the cover glass 106 and display screen 104. In some cases, the touch sensing layer is applied to display screen 104 while in other cases the touch sensing layer is applied to cover glass 106. The touch sensing layer may for example be attached to the inner surface of cover glass 106. The touch sensing layer generally includes a number of sensors that are configured to activate as a user's finger touches the upper surface of cover glass 106. In the simplest case, an electrical signal is produced each time the finger passes a sensor. The number of signals in a given time frame may indicate location, direction, speed and acceleration of the finger on the touch sensitive portion, i.e., the more signals, the more the user moved his or her finger. In most cases, the signals are monitored by an electronic interface that converts the number, combination and frequency of the signals into location, direction, speed and acceleration information. This information may then be used by the portable electronic device 10 to perform the desired control function relative to the display screen 104.

Described herein are improved methods for curing LOCAs between substrates. Methods for detecting uncured LOCA between substrates using a probe are described. In addition, improved methods for curing a laminated stack which includes a pre-curing process are described. In addition, an improved light emitting diode (LED) unit assembly for exposing a laminated stack up to ultraviolet (UV) light during a pre-curing process is described. A method for testing the LED unit assembly prior to a pre-curing process is described.

Figure 2A:
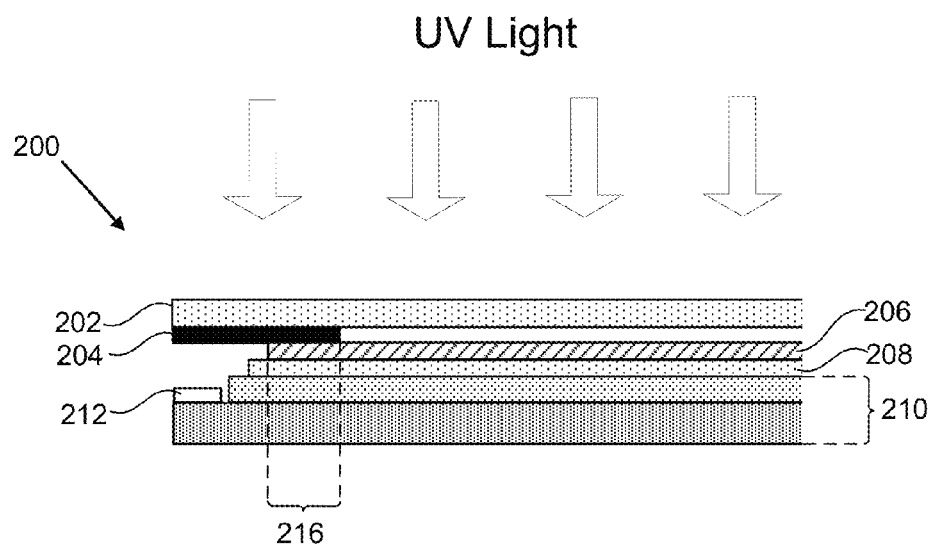
FIG. 2A shows a laminated stack up which includes a liquid optically clear adhesive (LOCA) during an ultraviolet (UV) curing application.

FIG. 2A shows a laminated stack up 200 which includes a liquid optically clear adhesive (LOCA) 206 in an ultraviolet (UV) curing application. In one embodiment, the laminated stack up 200 can include a cover glass 202, paint or ink layer 204, sensor layer 208, contact 212 and liquid crystal display (LCD) stack up 210. Cover glass 202 can be formed of glass, a polymer or other suitable substrate. In some embodiments, LCD stack up can include one or more additional sensor layers, a charge coupled device (CCD), a back light unit, one or more filters and underlying LCD. In the laminated stack up 200, LOCA 206 is disposed between cover glass 202 and sensor layer 208 to adhere the two layers together. Additional layers of LOCA can be used to adhere other layers of LCD stack up 210 together. For simplicity, only LOCA 206 is shown. UV light can be shown down on laminated stack up 200 to cure LOCA 206 and adhere cover glass 202 to sensor layer 208. Suitable LOCA types can include, for example, acrylic-based and silicone-based LOCA types. The LOCAs can be UV curable as well as heat and/or moisture curable.

As shown in FIG. 2A, ink layer 204 is generally used as a cosmetic application to hide underlying features from the view of a user's perspective on top of cover glass 202. As shown, ink layer 204 can block portion 216 of LOCA 206 from exposure to UV light during a curing process. If LOCA 206 is heat sensitive, portion 216 of LOCA 206 can experience less heat since it is not as exposed to UV light as a heat source. As such, portion 216 of LOCA 206 can remain uncured and remain in a partially liquid state. Since the physical properties, i.e., viscosity of LOCA 206 will be different in portion 216 covered by ink layer 204 compared to the remaining portion of LOCA 206, a boundary of cured and uncured LOCA can be formed and remain after all of LOCA 206 is cured and in solid state. This boundary can produce an undesired wavy appearance of LOCA 206 in the proximity of ink layer 204. In addition, because portion 216 of LOCA 206 can remain in a partial liquid state, portion 216 can migrate to different portions of laminated stack up 200, as shown in FIG. 2B.

Figure 2B:
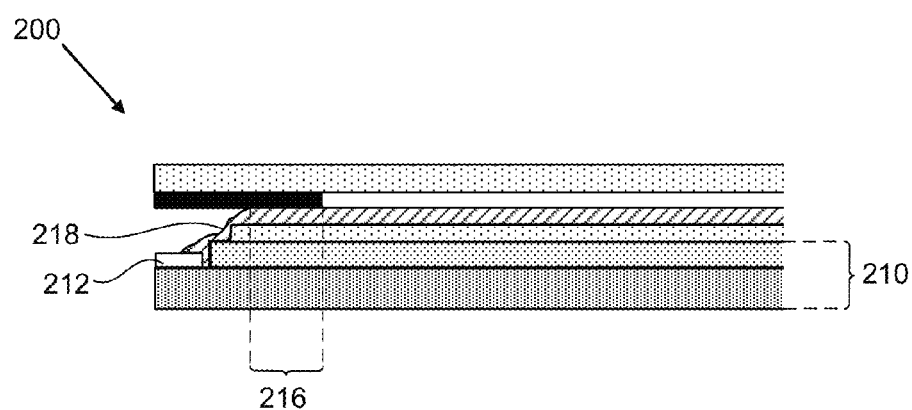
FIG. 2B shows the laminated stack up of FIG. 2A after UV curing with an overflow portion of LOCA.

FIG. 2B shows laminated stack 200 after UV curing. Since portion 216 of LOCA 206 remained partially uncured and in liquid state during the UV curing operation of FIG. 2A, portion 216 of LOCA 206 was allowed to migrate forming an overflow portion 218. As shown, overflow portion 218 of LOCA 206 can cover surfaces of sensor layer 208, LCD stack up 210 and partially cover contact 212. Since contact 212 is configured to make electrical contact with wires or components, overflow portion 218 of LOCA can inhibit the ability of contact 212 to make an electrical connection with the wire or component.

In order to avoid the undesired wavy appearance and overflow occurrence described above, embodiments described herein provide methods to detect uncured LOCA between substrates during a manufacturing process of a laminated stack such as laminated stack 200 of FIGS. 2A and 2B. In one embodiment, a probe or shim is provided that can be inserted in between the substrates after a curing process in order to detect the presence of uncured LOCA.

FIG. 3 shows one embodiment of a probe 300 configured to detect uncured LOCA in accordance with described embodiments. Probe 300 is suitably thin so that it can be inserted between two substrates that are being adhered together using LOCA, such as the cover glass 202 and sensor layer 208 of FIGS. 2A and 2B. In the embodiment shown in FIG. 3, probe 300 has a main portion 302 that has a length 310 and a probe end 304 that has a length 312. During insertion, probe end 304 can be inserted to a depth defined by depth line 306. Depth line 306 can be marked or unmarked on probe 300. Marking can be indicated using, for example, a line marking. In some embodiments, depth line 306 can be indicated by a color change in probe 300. That is, main portion 302 can be a different color than probe end 304. After insertion to the predetermined depth is complete, probe 300 can be extracted and inspected for the presence of uncured LOCA. Since uncured LOCA is in liquid or partial liquid state, the uncured LOCA can stick to the surfaces of probe 300 upon contact. The presence of liquid or partial liquid LOCA on probe 300 can be an indication of uncured LOCA between the substrates.

Probe 300 can be made of any suitable material for insertion between the substrates as described herein. In preferred embodiments, probe 300 is made of a material that allows LOCA to adhere to it upon contact. In some embodiments, probe 300 is made of a flexible material such as a thermoplastic polymer resin such as polyethylene terephthalate (PET). Probe 300 can have any suitable dimensions for inserting between substrates. Probe end 304 preferably has an end thickness suitably small to fit between blocked portions of the substrates yet suitably large so as to get an accurate account of any uncured LOCA. Main portion length 310 and width 308 can be of a suitable size for a person or robot to insert and extract probe 300 between the substrates. In one embodiment, main portion length 310 is about 40-50 mm, main body width 308 is about 10-20 mm and probe end length 312 is about 2-3 mm. In some embodiments, probe 300 can have different thicknesses along its length. For example, probe end 304 can be thinner than main portion 302 so that it can be thin enough to fit between substrates. In one embodiment, probe end 304 thickness is about 25-100 microns and main portion 302 thickness is about 100-200 microns.

FIG. 4 shows another embodiment of a probe 400 also configured to detect uncured LOCA. In the embodiment shown in FIG. 4, probe 400 has a main portion 402 that has a length 410 and a probe end 404 that has a length 412. During insertion, probe end 404 can be inserted to a depth defined by depth line 406. Depth line 406 can be marked or unmarked on probe 400. Marking can be indicated using, for example, a line marking or a color change in probe 400. As shown, probe 400 is tapered at probe end 404. Tapered portion 404 can taper from a main portion width 408 to a probe end width 414. In some cases, depth line 406 is located at the start of the tapering of tapered portion 404. In this way, depth line 406 can easily be identified without otherwise marking probe 400. That is, probe 400 can be inserted to a depth indicated by the start of tapered portion 404.

Probe 400 can have any suitable dimensions for inserting between substrates. Probe end 404 preferably has an end width 414 suitably small to fit between blocked portions of the substrates yet suitably large so as to get an accurate account of any uncured LOCA. Main portion length 410 and width 408 can be of a suitable size for a person or robot to insert and extract probe 400 between the substrates. In one embodiment, main portion length 410 is about 40-50 mm, main body width 408 is about 10-20 mm and probe end length 412 is about 2-3 mm. In some embodiments, probe 400 can have different thicknesses along its length. For example, probe end 404 can be thinner than main portion 402 so that it can be thin enough to fit between substrates. In one embodiment, probe end 404 thickness is about 25-100 microns and main portion 402 thickness is about 100-200 microns.

Figure 5:
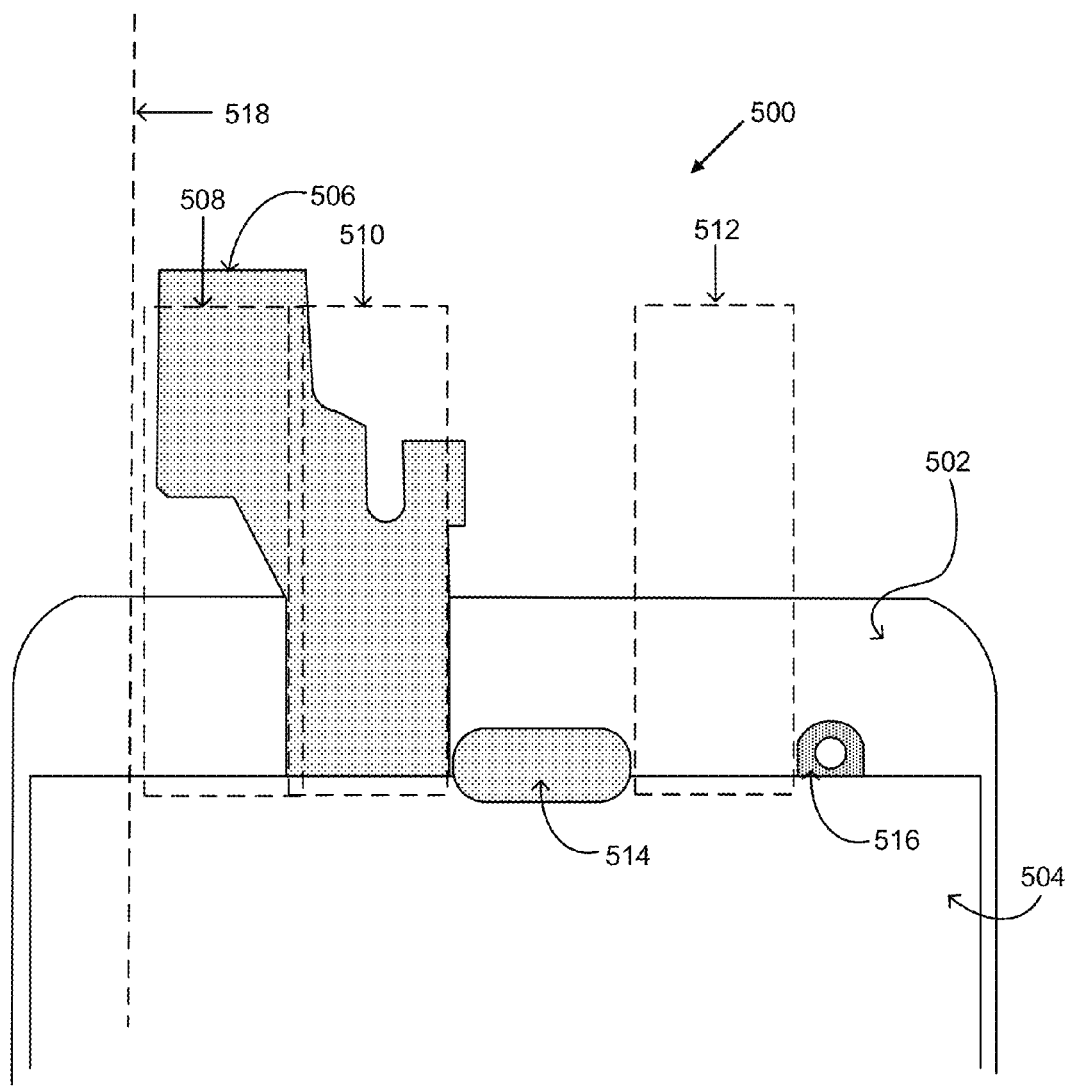
FIG. 5 shows a portion of a cover glass assembly for a portable electronic device indicating locations for inserting an uncured LOCA detection probe.

As described above, the detection probe described herein can be used to detect uncured LOCA between substrates as part of a display screen for an electronic device. FIG. 5 shows a portion of a cover glass assembly 500 for a portable electronic device. Cover glass assembly 500 includes frame 502, laminated stack up 504, flex circuit 506, screw fixture 516 and speaker mesh cover 514. During assembly, cover glass assembly 500 can be attached to a main housing unit of a portable electronic device. Laminated stack up 504 can include a number of layers with each adhered to each other using LOCA. For example, laminated stack up 504 can include a cover glass, an ink layer, a display sensor layer, a touch sensor layer and an LCD. After a curing process, a probe can be inserted between layers that have LOCA disposed between them to test for the existence of any uncured LOCA. FIG. 5 shows possible probe insertion locations 508, 510 and 512. As shown, insertion locations 508, 510 and 512 can be chosen by physical restraints of features of the cover glass assembly 500, for example, screw fixture 516 and speaker mesh cover 514. Dashed line 518 indicates an additional restriction where a probe should not interfere with portions of the LOCA associated with gap fill for the cover glass assembly 500. The probe(s) can be used to probe LOCA between different substrates in laminated stack up 504. For example, insertion location 510 can be used to probe LOCA between a display sensor layer and a touch sensor layer and insertion locations 508 and 512 can be used to probe LOCA between the cover glass and a sensor layer associated with flex circuit 506. In this way, multiple LOCA locations applied between different substrates in laminated stack up 504 can be tested for uncured LOCA after curing. In one embodiment, the same probe can be used a number of times by cleaning the probe between each insertion.

In a manufacturing setting where numerous laminated pieces are being manufactured, it can be advantageous to quantify the depth of uncured LOCA. For example, in certain applications or product lines it can be acceptable to have a certain amount of uncured LOCA after the curing process. In the lamination stack in FIGS. 2A and 2B, for example, it may be acceptable to have a certain amount of uncured LOCA as long as the uncured LOCA does not produce an undesired wavy appearance or overflow onto critical portions of the lamination stack. In these cases, it can be advantageous to have a calibrated probe, such as probe 400 shown in FIGS. 6A-6C.

Figure 6A:
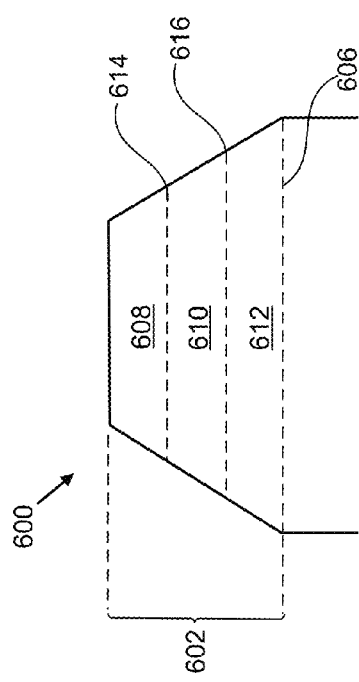
FIGS. 6A-6C show a close up view of a calibrated probe used to detect amounts of uncured LOCA between substrates.
Figure 6C:
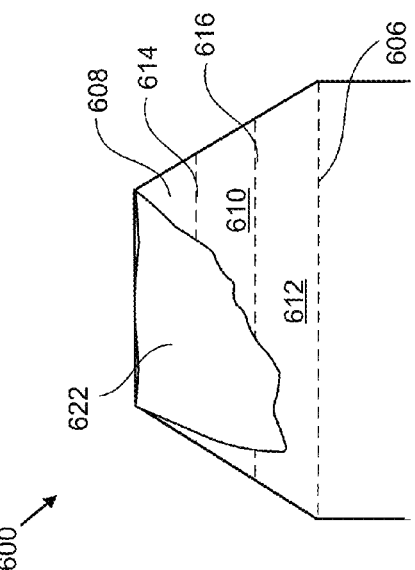
Figure 6B:
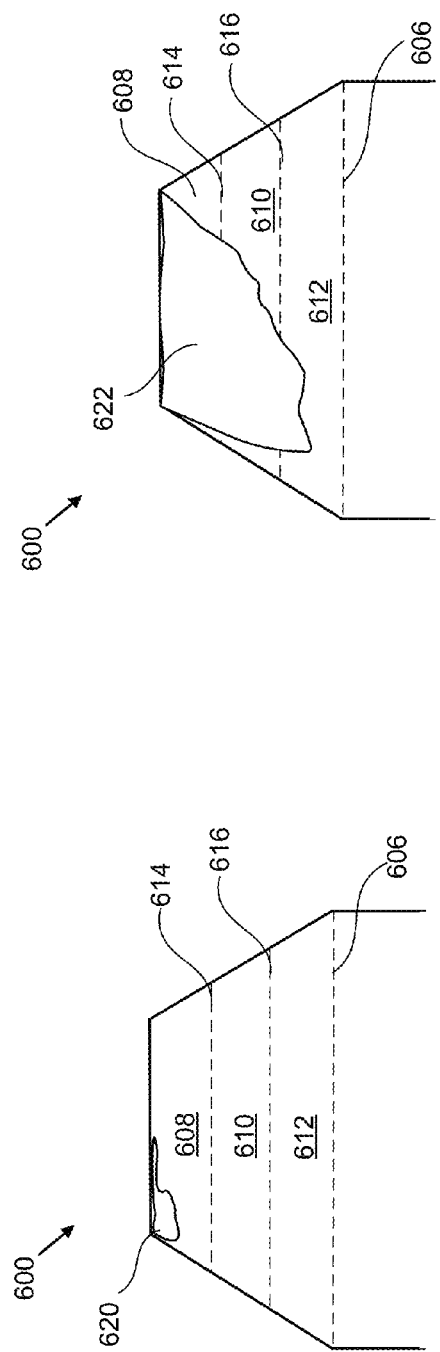

FIG. 6A shows a close up view of tapered portion 602 of probe 600. In some embodiments, depth line 606 can be defined by the start of the taper of tapered portion 602. In some embodiments, depth line 606 can marked by a line marking or a color change in probe 600. As shown, tapered portion 602 includes calibrated regions 608, 610 and 612 separated by boundary lines 614 and 616. In some embodiments, calibrated regions 608, 610 and 612 can be distinguished by line markings at boundary lines 614 and 616. In some embodiments, calibrated regions 608, 610 and 612 are distinguishable by having different colors. When probe 600 is inserted between two substrates and extracted, uncured LOCA can adhere and be visible on probe 600 at different locations along calibrated regions 608, 610 and 612 depending upon the depth of the uncured LOCA. In this way, the use of the calibrated probe 600 can allow a more accurate detection of the amount of uncured LOCA that may exist between the substrates, which can be an indication of how likely the uncured LOCA will cause an undesired wavy appearance or overflow problems. FIGS. 6B and 6C illustrate examples of probe 600 having different depths and amounts of uncured LOCA.

FIG. 6B shows probe 600 after insertion between two substrates in a laminated stack up. As shown, uncured LOCA 620 adheres to a portion of probe 600 confined within calibrated region 608. That is, the detectable depth of uncured LOCA 620 does not go past boundary line 614. In some applications, uncured LOCA 620 confined within region 608 can be acceptable. For example, uncured LOCA confined to region 608 may not cause an undesired wavy appearance or overflow problems. FIG. 6C shows probe 600 after it has been cleaned and inserted between two other substrates in a laminated stack up. As shown, the amount of uncured LOCA 622 adhering to probe 600 extends beyond boundary lines 614 and 616 and into calibrated region 612. In some applications, uncured LOCA 622 extending past boundary line 614 or 616 can be unacceptable. For example, uncured LOCA 622 extending past these boundary lines can indicate a high probability of an undesired wavy appearance or overflow problems in the resultant stack up. As such, the laminated stack up showing uncured LOCA 622 may be reworked or removed from the production line.

In a production line setting, a binning technique can be used to distinguish between laminated stacks that have acceptable and unacceptable amounts of uncured LOCA. As an example, Table 1 below shows process controls for a binning technique that can be used to determine acceptable and unacceptable amounts of uncured LOCA based on insertion locations and calibration regions. As shown in Table 1, laminated stacks having no uncured LOCA or uncured LOCA confined to calibration region 1 are acceptable and can be kept and moved forward to subsequent processing. Laminated stacks probed at insertion location 2 having uncured LOCA in calibration regions 2 and 3 are unacceptable and should be discarded or reworked. Laminated stacks probed at insertion locations 1 and 3 having uncured LOCA in calibration region 3 are unacceptable and should be discarded or reworked.

TABLE 1

|  | Insertion Location 1 | Insertion Location 2 | Insertion Location 3 |
| --- | --- | --- | --- |
| No Uncured LOCA | keep | keep | keep |
| Calibration Region 1 | keep | keep | keep |
| Calibration Region 2 | keep | discard/rework | keep |
| Calibration Region 3 | discard/rework | discard/rework | discard/rework |

Figure 7:
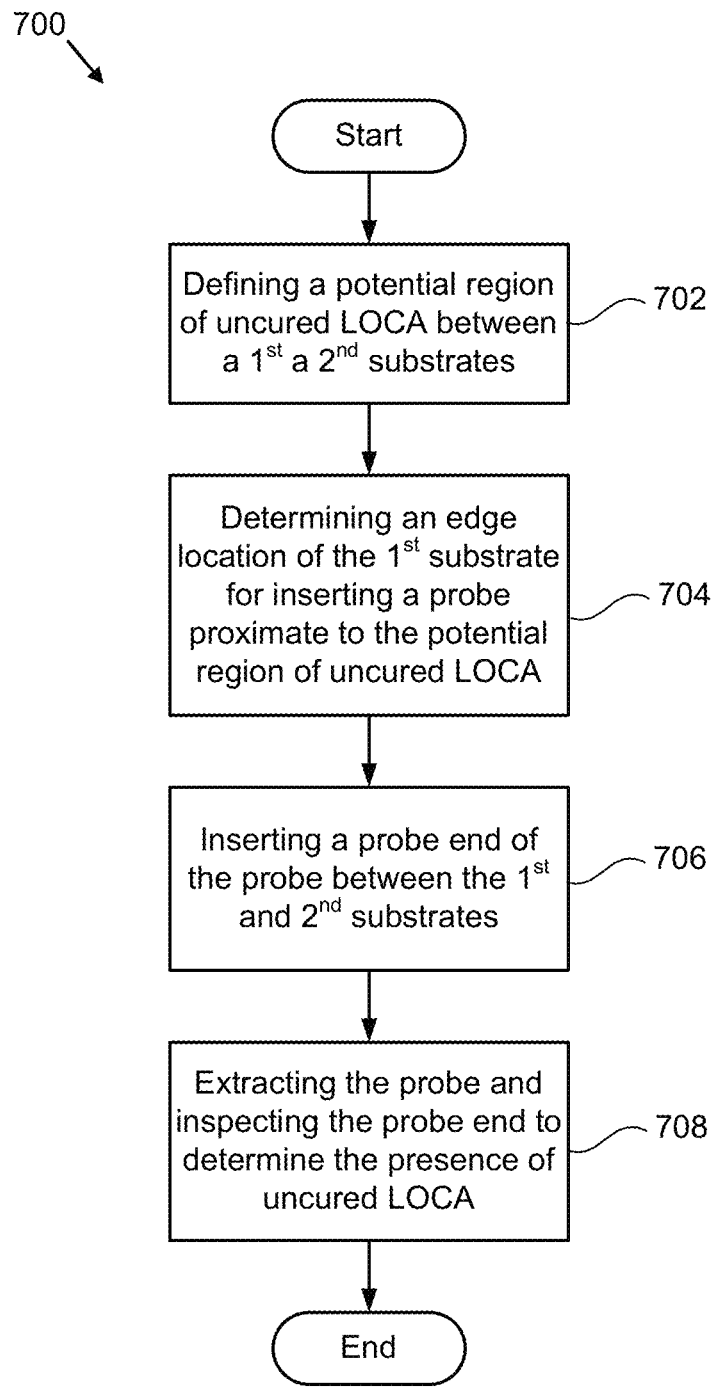
FIG. 7 shows a flowchart showing steps involved in the detection of uncured LOCA between a first and second substrate.

FIG. 7 shows a flowchart 700 showing steps involved in the detection of uncured LOCA between a first and second substrate. At 702, a potential region of uncured LOCA between a first substrate and a second substrate is defined. As discussed above with respect to FIGS. 2A and 2B, the regions may be regions of a laminar stack where the LOCA is exposed to less UV light. At 704, an edge location of the first substrate for inserting a probe proximate to the potential region of uncured LOCA is determined. The edge location can be chosen based in part on physical restraints of the surrounding features. For example in FIG. 5, insertion locations 508, 510 and 512 for laminated stack up 504 are chosen in part due to physical restraints due to the location of screw fixture 516, speaker mesh cover 514 and gap fill portion 518. At 706, a probe end of the probe is inserted between the first and second substrates. As describe above, the probe end can tapered and be thinner than the probe main portion. At 708, the probe is extracted and the probe end is inspected to determine the presence of uncured LOCA. As described above, the probe end can be calibrated to identify the depth and amount of uncured LOCA.

During a typical manufacturing process, a LOCA is applied onto a substrate and the substrate is aligned and attached onto another substrate under ambient or vacuum conditions. The attached substrates are then temporarily fixed by curing the LOCA during a "pre-curing" step. The pre-curing process can fix the position of the substrates and keep them from moving around prior to a curing process. After pre-curing, a visual inspection can be conducted to check the quality of the adhesive bond. If the bond is defective (e.g. bubbles, foreign particles, mis-alignment, etc.), in some cases the substrates can be taken apart and adhesive is cleaned off using a solvent. After cleaning, the substrates can be re-assembled. If there is no defect in the bond, the module will go through a final curing step to fully cure the adhesive bond between the substrates.

In some embodiments, a UV pre-curing process is used. In some cases, a portion of the laminated structure is exposed to UV light to fix that portion together prior to a final UV curing where the entire laminated structure is exposed to UV light. For example, in the portable electronic device 10 of FIG. 1, in one embodiment the edge around the perimeter of display screen 104 is exposed to UV light during a pre-curing process to fix display screen 104 to cover glass 106. Then, in a subsequent curing process, the entire area of display screen 104 is exposed to UV light. To accomplish this, a UV mask or filter can be used during the pre-curing process to block interior portions of display screen 104 from UV light.

Figure 8A:
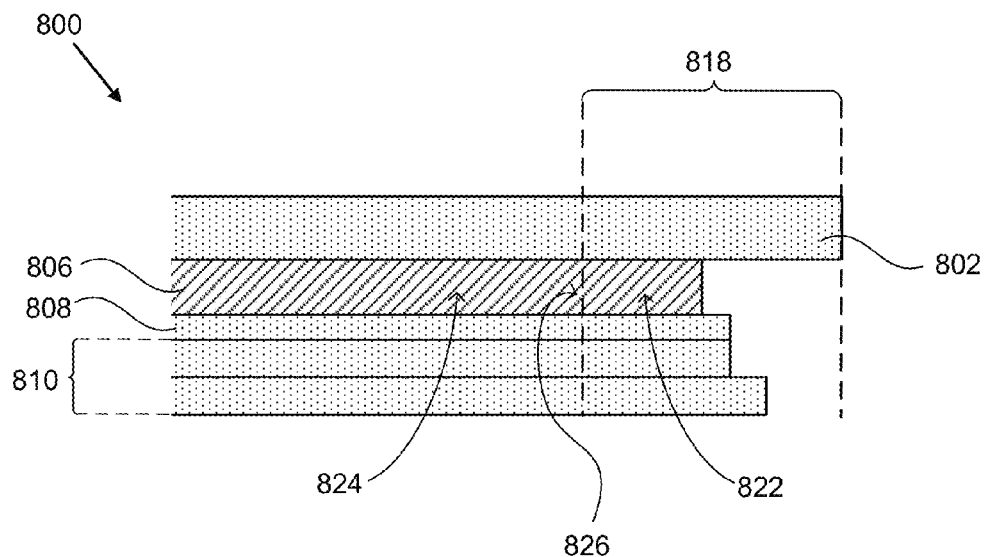
FIGS. 8A and 8B show a close-up view of a laminated stack up during pre-curing and curing processes.

FIG. 8A shows a close-up view of a laminated stack up 800 during a pre-curing process and a curing process. LOCA 806 is disposed between cover glass 802 and sensor layer 808. For simplicity, an ink layer used in some laminated stack ups is not shown. LCD stack up 810 is disposed below sensor layer 808. During a pre-curing process, area 818 of laminated stack up 800 corresponding to the perimeter of sensor layer 808 and LCD stack up 810 is exposed to UV light. Area 818 is left unmasked during the pre-curing process while the remainder of laminated stack up 800 is masked using a mask. As a result of the pre-curing process, portion 822 of LOCA 806 becomes at least partially cured and hardened while portion 824 of LOCA 806 remains substantially uncured and in liquid form. Due to the different physical states of the hardened portion 822 and liquid portion 824 of LOCA 806, liquid portion 824 can migrate into hardened portion 822. This can cause the formation of a visible line at boundary 826 between hardened portion 822 and liquid portion 824 of LOCA 806. After the pre-curing process is complete, the mask is removed and the entire laminated stack up 800 is exposed to UV light. As a result, portion 824 becomes cured and hardened. However, the visible line at boundary 826 between hardened portion 822 and liquid portion 824 of LOCA 806 can still remain, causing an unappealing appearance.

One possible way to avoid the formation of the visible line at boundary 826 between hardened portion 822 and liquid portion 824 of LOCA 806 is to minimize the time period between the pre-curing and curing processes (referred to as post pre-cure time). This can minimize the occurrence of migration of LOCA in liquid form to the hardened or partially hardened portions of LOCA. The minimized post pre-cure time can be determined based on a number of factors such as the UV light intensity, LOCA type and the stack up composition (e.g., types and thickness of substrates). However, in a manufacturing setting the opportunity to minimize post pre-cure time may be limited due to production line demands.

Figure 8B:
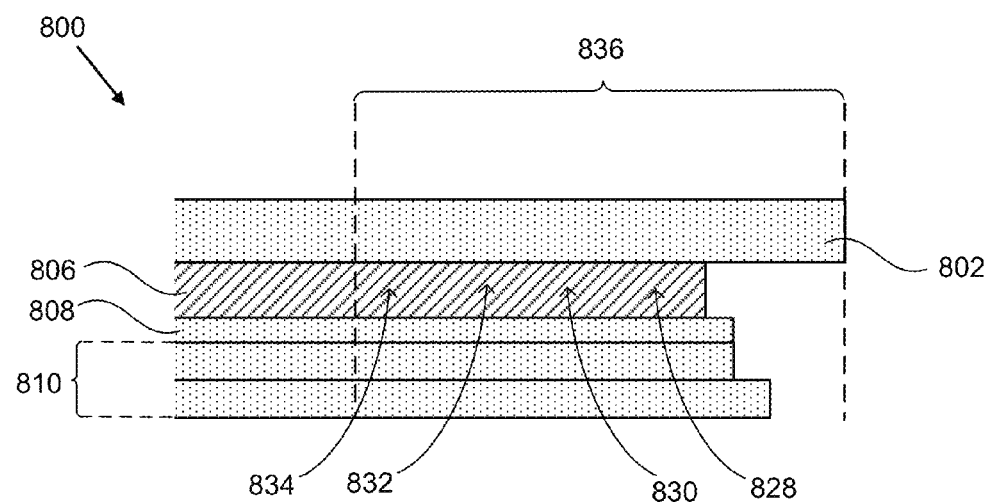

Other methods for avoiding the formation a visible line between pre-cured and cured regions of LOCA will now be described. Methods involve varying the exposure of different portions of the LOCA to UV light during the pre-curing process. To illustrate, FIG. 8B shows a close-up view of the laminated stack up 800 during a pre-curing process involving a variable UV exposure. During a variable exposure pre-curing process, different portions of LOCA 806 will experience different amounts of UV exposure. For example, portion 828 can experience more UV exposure than portion 830, which can experience more UV exposure than portion 832, which will experience more UV exposure than portion 834. In this way, portion 836 of LOCA 806 can have gradual gradient of partially cured LOCA. The result is no sharp boundary line between hardened portions and liquid portions of LOCA 806.

Figure 9A:
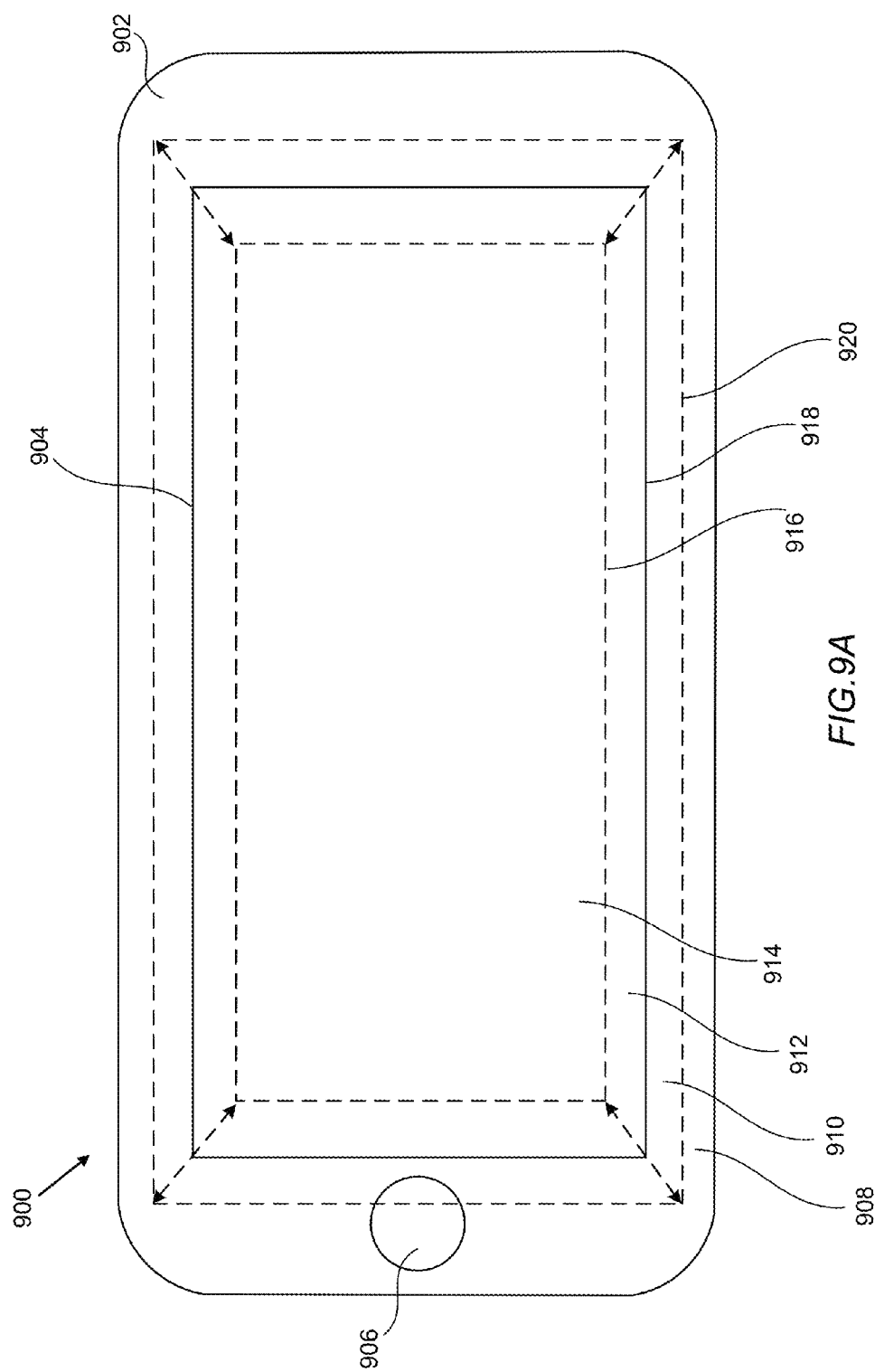
FIGS. 9A-9C show top views of a portable electronic device during variable UV exposure pre-curing processes in accordance with described embodiments.

To accomplish the varied UV exposure of LOCA 806 during the pre-curing process described above, a number of techniques can be used. In one embodiment, a moving shutter or shutters can be used to block different portions of area 836 at different times. To illustrate, FIG. 9A shows a top view of a portable electronic device 900 during a pre-curing process in accordance with an embodiment described herein. Portable electronic device 900 includes cover glass 902, hole 906 to accommodate a user clickable input button and display screen 904. Movable shutter or shutters can be positioned over portable electronic device 900 to allow variable UV exposure to different portions of cover glass 902, display screen 904, underlying stacks of substrates as part of display screen 904 and UV sensitive LOCA used to bind the substrates together. The movable shutter or shutters can be part of a UV light assembly or a movable mask that is placed between the UV light source and electronic device 900. At time 1, the shutters are configured to open to a position 920 to allow portion 908 of electronic device 900 to be exposed to UV light. As a result, the portion of LOCA corresponding to portion 908 is at least partially cured/hardened. At time 2, the shutters are configured to open to a position 918 to allow portions 908 and 910 of electronic device 900 to be exposed to UV light and for corresponding portions of LOCA to be at least partially cured/hardened. At time 3, the shutters are configured to open to a position 916 to allow portions 908, 910 and 912 of electronic device 900 to be exposed to UV light and for corresponding portions of LOCA to be at least partially cured/hardened. Note that portion 914 of electronic device 900 is typically not exposed during the pre-curing process but can be exposed during a subsequent full or final curing process. Since the exposure of UV light is gradually increased over regions 908, 910 and 912, there is no visible line between boundaries of LOCA exposed to pre-curing and curing processes.

Figure 9B:
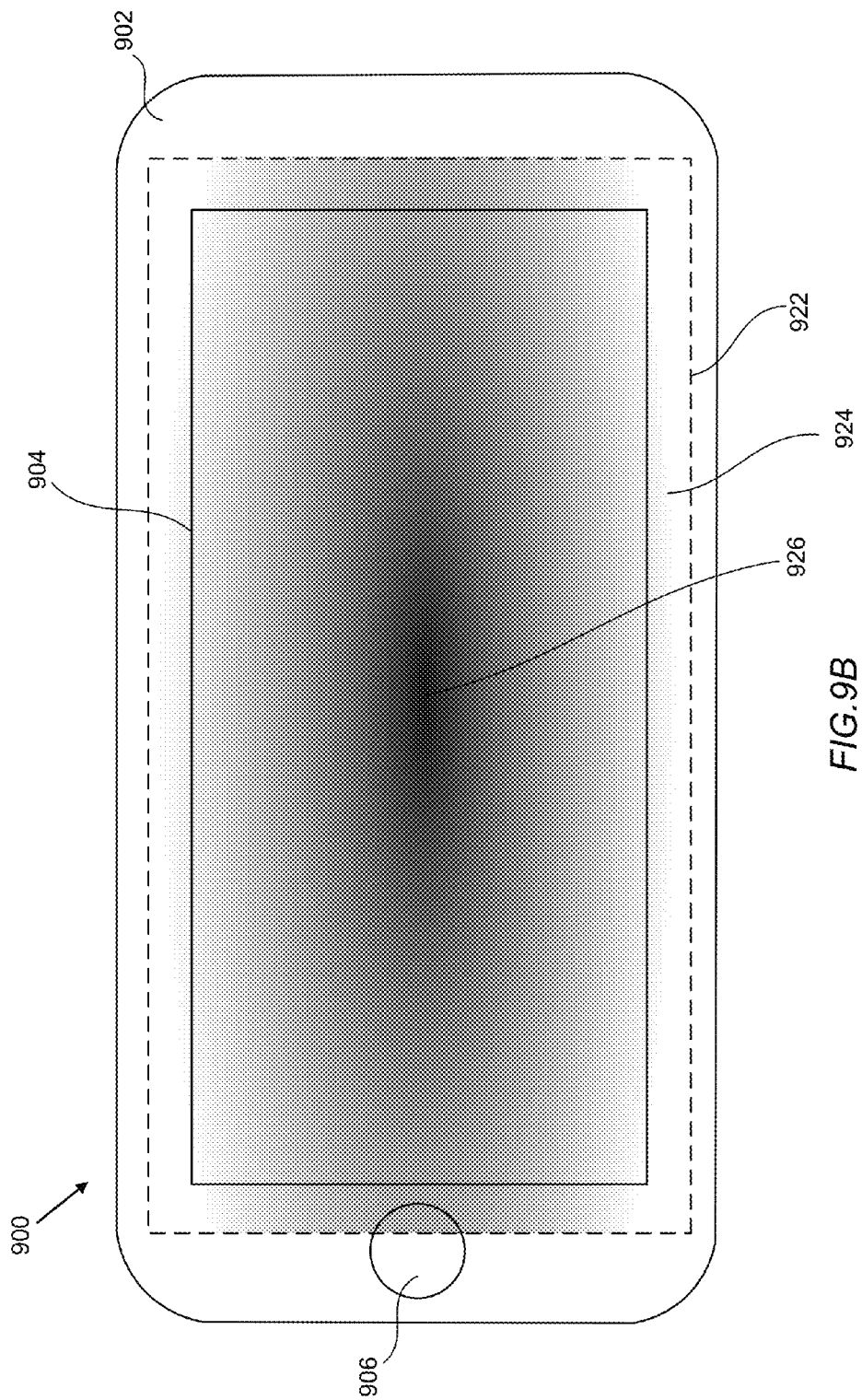

In another embodiment, a gradient filter is used to accomplish varied UV exposure to a LOCA. FIG. 9B shows a top view of a portable electronic device 900 during a pre-curing process using gradient filter 922. Gradient filter 922 is an optical filter that is partially covered with ink or other opaque material that does not allow UV light to pass. The density of opaque material gradually varies from high density darker regions 926 to low density lighter regions 924. High density darker regions 926 allow little or substantially no UV light to pass and low density lighter regions 924 allow greater or substantially all of the UV light to pass. In one embodiment, the high density darker regions 926 allow substantially no UV light to pass and low density lighter regions 924 allow more UV light to pass than the high density darker regions 926 but less than the entire incident UV light to pass. As shown in the embodiment of FIG. 9B, the density of opaque material gradually decreases from high density darker regions 926 to low density lighter regions 924. Gradient filter 922 can be made of any suitable material such as glass or plastic. The embodiment of FIG. 9B shows high density darker regions 926 positioned at the central area of electronic device 900 and low density lighter regions 924 around the outside perimeter of display screen 904. Since more UV light is able to pass through low density lighter regions 924 compared to high density darker regions 926, the corresponding underlying stacks of substrates as part of display screen 904 and UV sensitive LOCA used to bind the substrates together are exposed to more and less UV light, respectively. Thus, during a pre-curing process LOCA regions around the outside perimeter of display screen 904 are cured more than internal LOCA regions of display screen 904 with a gradual decrease of amount of curing in between. After the pre-curing process is complete, a full or final curing process can be conducted where the entire surface of the electronic device 900 can be exposed to the same dose of UV light. Since the exposure of UV light is gradually increased over LOCA regions, there is no visible line between boundaries of LOCA exposed to pre-curing and curing processes.

Figure 9C:
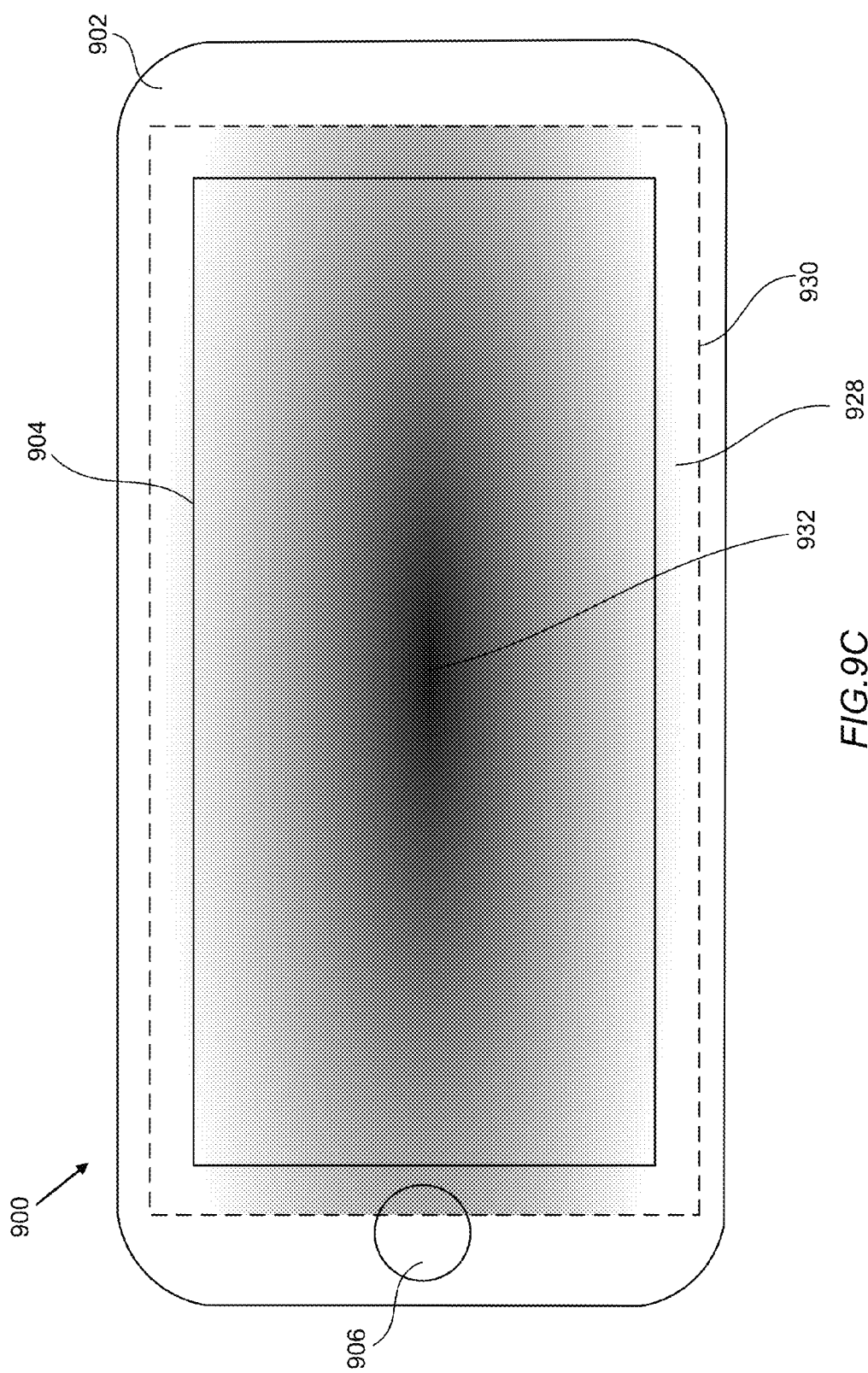

In another embodiment, a gradient porous mask is used to accomplish varied UV exposure to a LOCA. FIG. 9C shows a top view of a portable electronic device 900 during a pre-curing process using gradient porous mask 930. Gradient porous mask 930 is an opaque material that has a number of holes to allow UV light to shine through the holes. In some embodiments, the holes are small enough to allow UV light to scatter. The holes can be provided in the opaque mask using a number of suitable techniques including mechanical or laser drilling. Gradient porous mask 930 has regions 928 that have a high density of holes, thereby allowing more UV light to pass, and regions 932 that have a low hole density or no holes, thereby allowing little or no UV light to pass. In one embodiment, the low hole density regions 932 allow substantially no UV light to pass and high hole density regions 928 allow more UV light to pass than the low hole density regions 932 but less than the entire incident UV light to pass. Like gradient filter 922, gradient porous mask allows a gradual transition of regions that allow more light to pass to regions that allow less light to pass. That is, the density of holes decreases from high hole density regions 928 to low hole density regions 932. The embodiment of FIG. 9C shows regions 932 which allow little or no UV light to pass positioned at the central area of electronic device 900 and regions 928 which allow more light to pass positioned around the outside perimeter of display screen 904. Since more UV light is able to pass through regions 928 compared to regions 932, the corresponding underlying stacks of substrates as part of display screen 904 and UV sensitive LOCA used to bind the substrates together are exposed to more and less UV light, respectively. Thus, during a pre-curing process LOCA regions around the outside perimeter of display screen 904 are cured more than internal LOCA regions of display screen 904 with a gradual decrease of amount of curing in between. After the pre-curing process is complete, a full or final curing process can be conducted where the entire surface of the electronic device 900 can be exposed to the same dose of UV light. Since the exposure of UV light is gradually increased over LOCA regions, there is no visible line between boundaries of LOCA exposed to pre-curing and curing processes.

Figure 10:
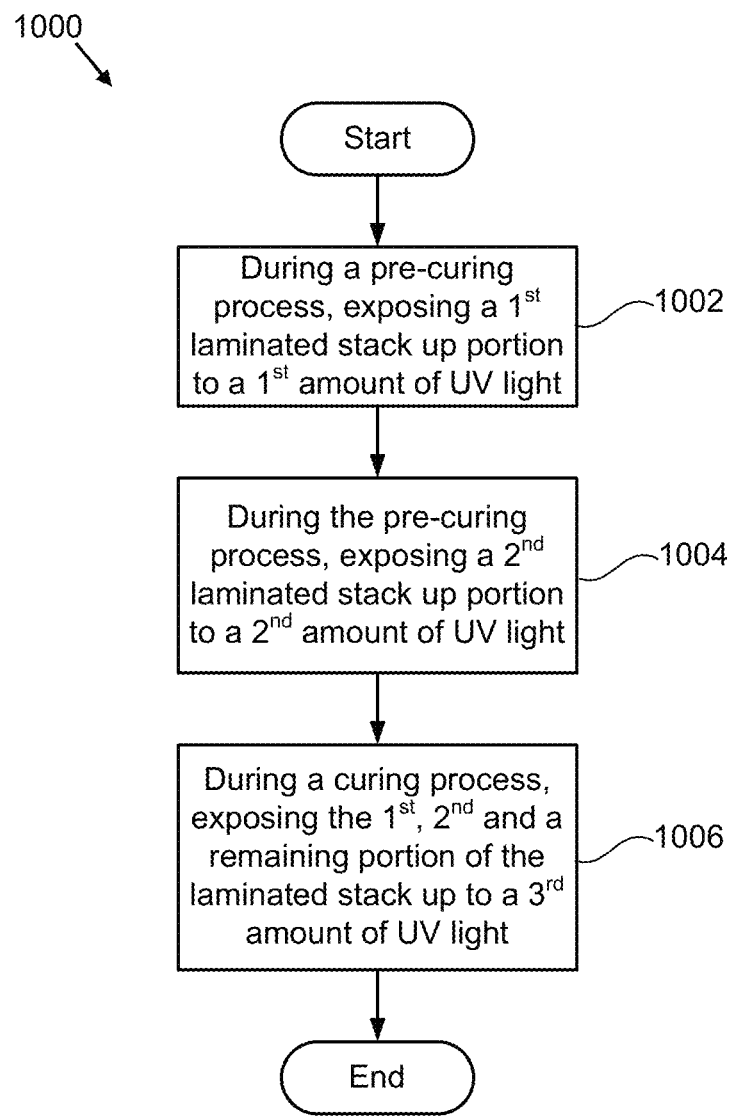
FIG. 10 shows a flowchart showing steps involved for curing LOCA between a first substrate and a second substrate involving pre-curing and curing processes.

FIG. 10 shows a flowchart 1000 showing steps involved for curing LOCA between a first substrate and a second substrate involving pre-curing and curing processes. The laminated stack up has a pre-curing area and a curing area. For example, in FIG. 9B, a pre-curing area can include areas that are substantially exposed to UV light during a pre-curing process, such as lighter regions 924. A curing area can include areas of the laminated stack up that are exposed to UV light during a full or final curing process, such as the entire cover glass area 902 of electronic device 900. At 1002, during the pre-curing process, a first portion of a laminated stack up is exposed to a first amount of UV light. As a result, a first LOCA portion corresponding to the first laminated stack up portion can become at least partially cured. In FIG. 9B, for example, the first portion can include the laminated stack up of electronic device 900 corresponding to lighter regions 924. At 1004, also during the pre-curing process, a second portion of a laminated stack up is exposed to a second amount of UV light. As a result, a second LOCA portion corresponding to the second laminated stack up portion can become at least partially cured. In FIG. 9B, for example, the second portion can include the laminated stack up of electronic device 900 corresponding to darker regions 932. At 1006, during a curing process, the first, second a remaining LOCA portion of the laminated stack up are exposed to a third amount of UV light. The remaining LOCA portion can correspond to that portion of LOCA in the laminated stack up that was not exposed to UV light during the pre-curing process. The remaining LOCA portion becomes at least partially cured due to exposure to the third amount of UV light. In FIG. 9B, for example, the remaining LOCA portion can include portions that were partially or fully blocked by gradient filter 922. Note that UV light source during the pre-curing and curing processes can be of the same or different intensities. For example, the pre-curing process can use a first UV light intensity and the curing process can use a second UV intensity. After the pre-curing and curing processes are complete, the transitions between the first, second and remaining LOCA portions are substantially non-visible.

Figure 11:
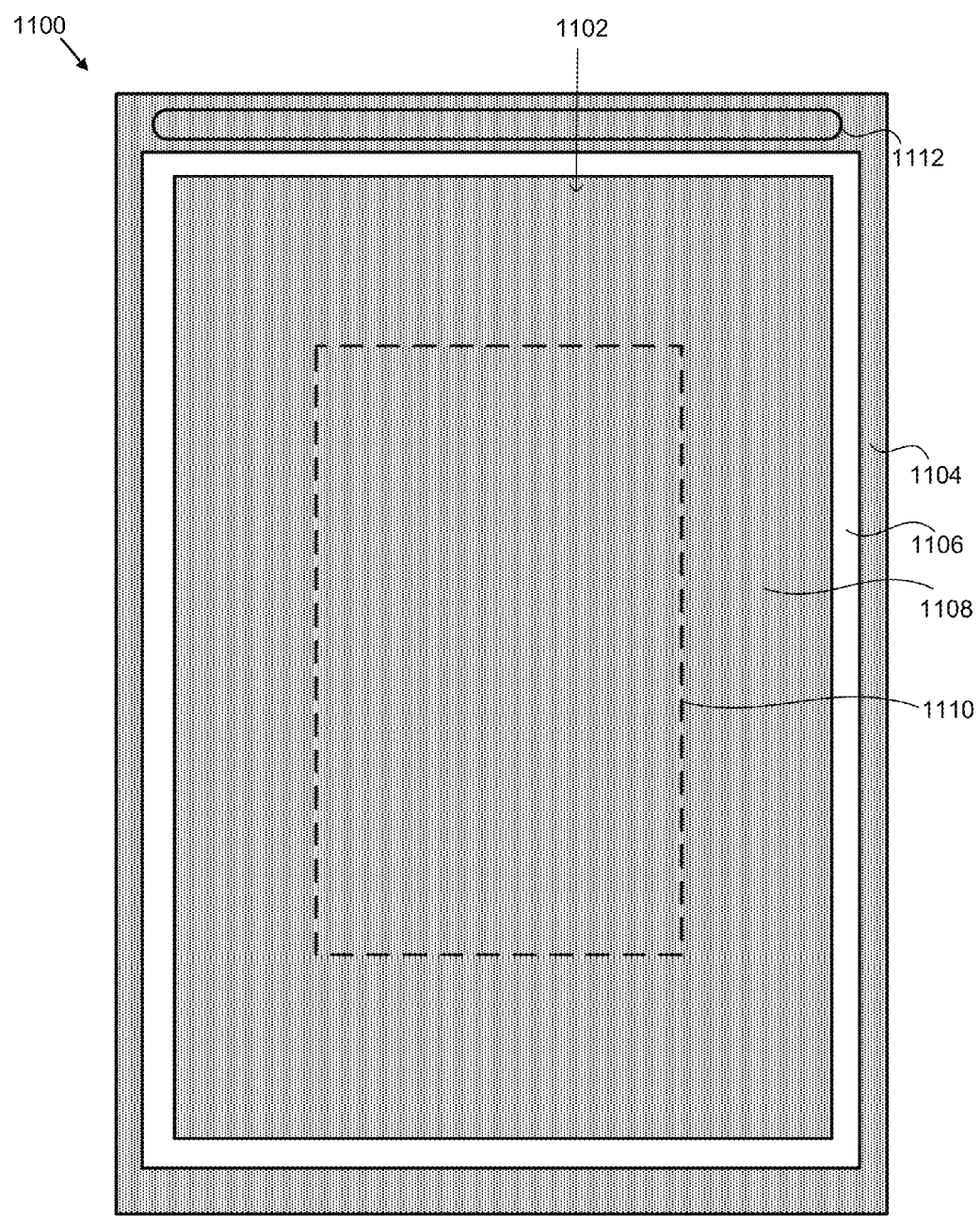
FIG. 11 shows a laminated stack up for a portable electronic device showing a pre-curing or dam area of a pre-curing process.

As described above, the pre-curing area can exist around a perimeter of the laminated stack up that is to be exposed to pre-curing and curing processes. FIG. 11 shows a laminated stack up 1100 for a portable electronic device in accordance with described embodiments. Laminated stack up 1100 includes cover glass (bottom of stack) and display screen 1110. In the embodiment of FIG. 11, mask 1102 includes opaque interior portion 1108 and opaque exterior portion 1104 that substantially block UV light from passing through and curing corresponding areas of LOCA in laminated stack up 1100 during a pre-curing process. Transparent portion 1106 of mask 1102 can allow UV light to pass through to and cure a corresponding area of LOCA in laminated stack up 1100 during a pre-curing process. The LOCA area corresponding to the transparent portion 1106 can be referred to as a pre-curing area or a dam area. As described above with reference to FIGS. 9A-9C, different regions of pre-curing area corresponding to transparent portion 1106 can be exposed to different amounts of UV light in order to reduce the occurrence of a visible line between pre-cured and cured regions of the LOCA. Feature 1112 is a component that has UV light reflective surfaces, such as a component with a metal surface. Note that in some cases, care should be taken to avoid the overlap of the pre-curing area with feature 1112 since feature 1112 can scatter UV light during the pre-curing process and cause inadvertent curing of portions of LOCA.

Figures 12A, 12B:
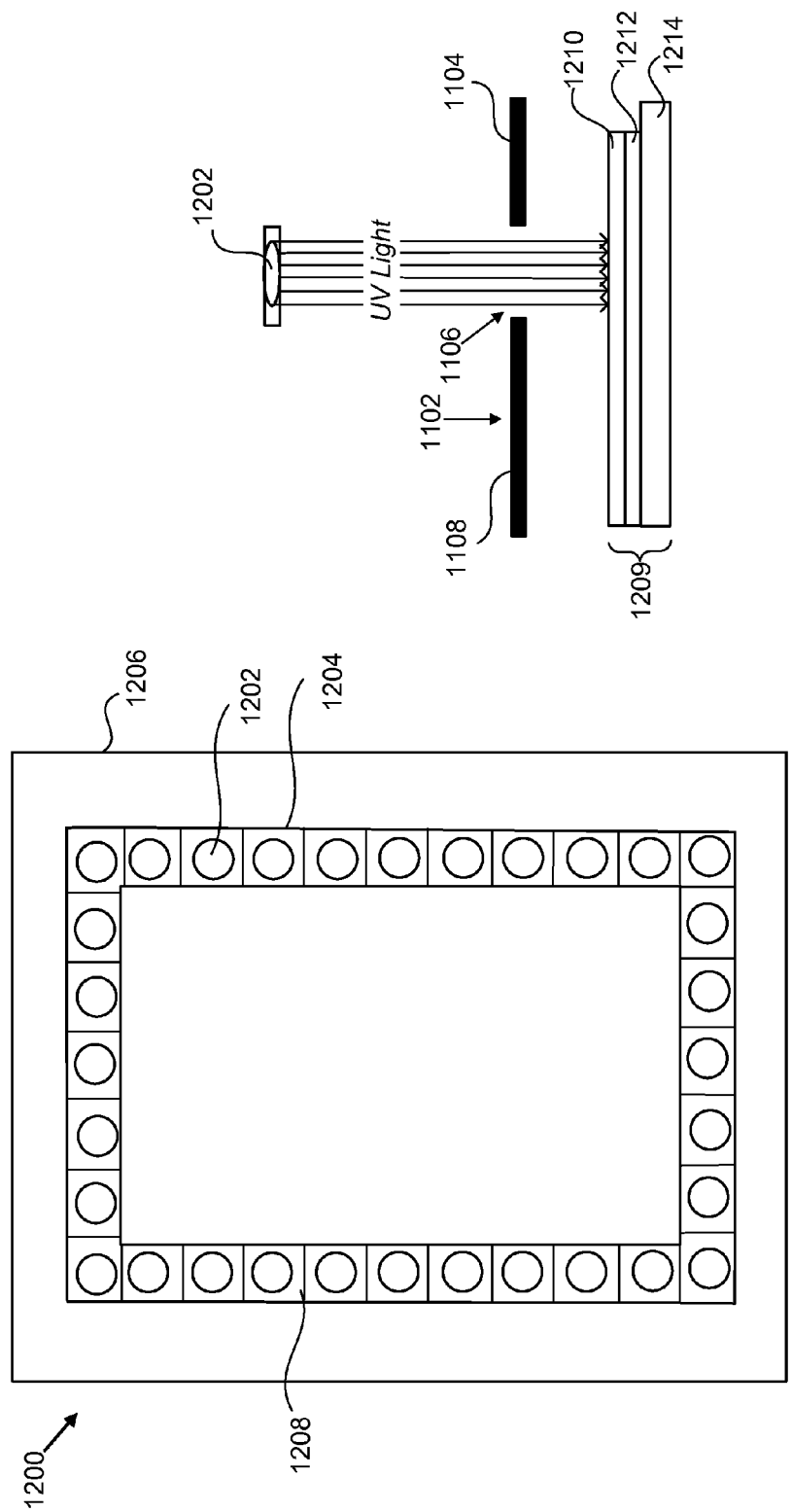
FIGS. 12A and 12B show a light emitting diode (LED) array used in a pre-curing process.

During the pre-curing process, the incident UV light is preferably directed substantially perpendicularly to the pre-curing area and not at an angle. This is because light that is incident on the laminated stack up at an angle can expose regions of the LOCA that are not directly underneath the opaque mask portions 1104 and 1108. The stray UV light can then cure portions of the LOCA that are not intended to be cured, which can cause visual defects in the LOCA and in the resultant laminated stack up after the pre-curing process. In order to avoid the occurrence of stray UV light exposure to unmasked portions of the laminated stack up, some embodiments described herein involve the use of a light emitting diode (LED) array source designed to direct substantially only perpendicular incident UV light on the laminated stack up. FIG. 12A shows a front view of a LED unit 1200 which includes an LED array 1208 that is shaped and sized to emit UV light that is substantially perpendicular to a pre-curing area, such as the pre-curing area corresponding to transparent portion 1106 of FIG. 11. LED unit 1200 includes LEDs 1202 arranged in a support structure 1204 that secures the LEDs 1202 in a particular arrangement within housing 1206. During a pre-curing process, LED unit 1200 can be positioned over a mask and a laminated stack up such that LEDs 1202 aligns with a transparent portion of the mask.

FIG. 12B shows a profile view of a portion of a laminated stack up 1209 undergoing a pre-curing process. Mask 1102 includes opaque interior portion 1108, opaque exterior portion 1104 and transparent portion 1106. Mask 1102 is positioned over laminated stack up 1209 during a pre-curing process. Laminated stack up 1209 includes a cover glass 1214, a sensor layer 1210 and LOCA 1212 positioned between cover glass 1214 and sensor layer 1210. In some embodiments laminated stack up 1209 can include additional sensor layers, LOCA layers and polarizing filter layers. LED 1202 is positioned in a substantially perpendicular arrangement relative to mask 1202 such that UV light that is emitted from LED 1202 impinges upon laminated stack up 1209 in a substantially perpendicular direction. This configuration can minimize the occurrence of stray UV light that can travel under portions of mask 1102 and expose portions of laminated stack up 1209 under opaque exterior portion 1104 and transparent portion 1106 of mask 1102. Stray light can be defined as light that is scattered, for example, by reflecting off of portions of mask 1102 or light that is entered non-perpendicularly through transparent portion 1106.

Figure 13:
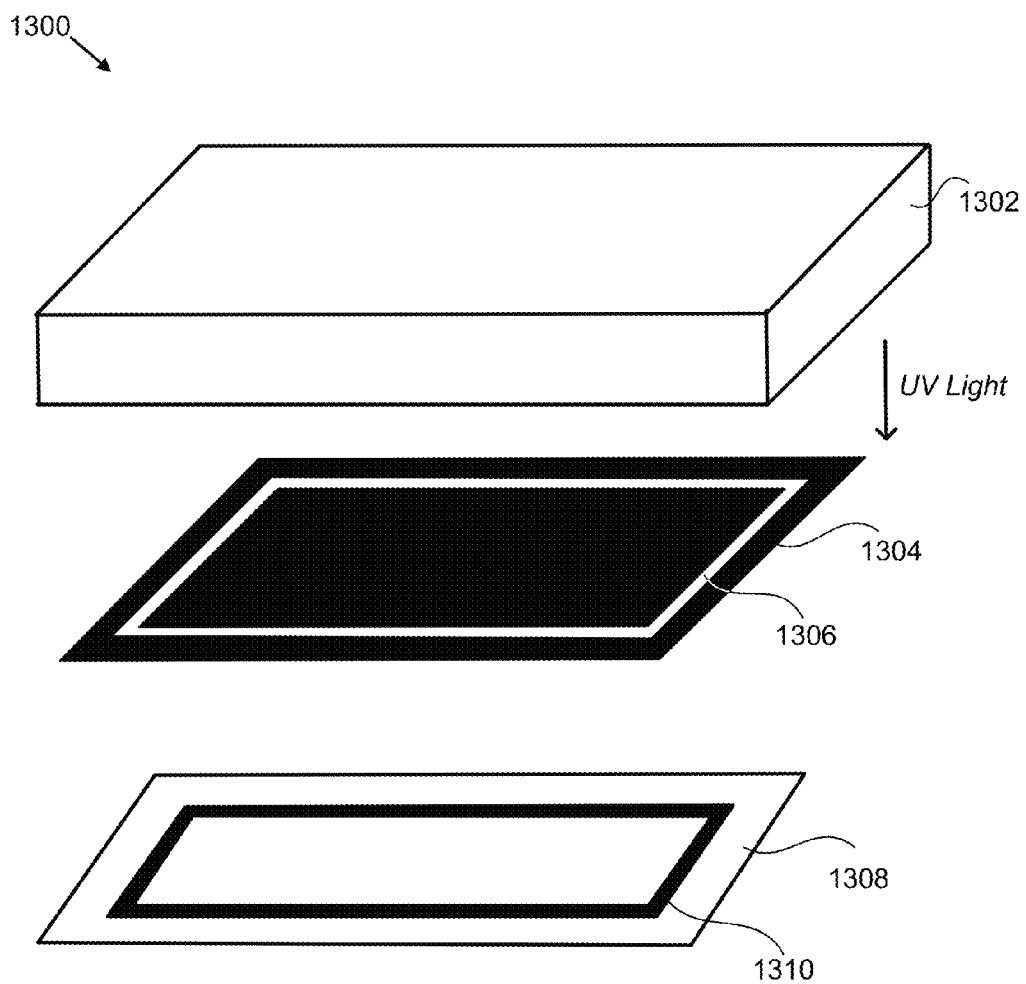
FIG. 13 shows a pre-curing test assembly for testing the positions of LEDs in a LED array prior to a pre-curing process.

In some cases, it can be desirable to test the positions of the LEDs in the LED array to make sure that the emitted UV light is substantially perpendicular to the mask and does not cause stray UV light to impinge upon undesired areas of a laminated stack positioned under the mask. For example, it can be desirable to align LEDs 1202 in FIG. 12A over transparent portions of an underlying mask in order to minimize scattering of light caused by light bouncing off portions of the underlying mask. FIG. 13 shows a pre-curing test assembly 1300 for testing the positions of LEDs prior to a pre-curing process. Pre-curing test assembly 1300 includes LED unit 1302, which is positioned over mask 1304, which is in turn positioned over UV sensitive paper 1308. LED unit 1302 is configured to have a number of LEDs (not shown) that can emit UV light.

In FIG. 13, the LEDs are arranged to closely correspond in shape to transparent portion 1306 of mask 1304. Transparent portion 1306 corresponds to the shape and size of a pre-curing area of a laminated stack up during a subsequent pre-curing process. During a testing process, LED unit 1302 is aligned over mask 1304 such that the LEDs in LED unit 1302 are positioned directly over transparent portion 1306. The LEDs are then turned on to allow UV light to pass through transparent portion 1306 and impinge upon UV sensitive paper 1308. As a result, imprint 1310 will appear on UV sensitive paper 1308. The shape and size of imprint 1310 can correspond to the shape and size of the impinging UV light that will impinge upon a laminated stack up during a pre-curing process. UV sensitive paper 1308 can be exposed a sufficient amount of time to produce a visible imprint 1310. In some embodiments, the UV sensitive paper is exposed to UV light for about the same amount of time as a subsequent pre-curing operation. After the UV sensitive paper is sufficiently exposed, UV sensitive paper 1308 can be inspected to ascertain whether imprint 1310 has a sufficiently clean outline to continue on to a pre-curing operation. For example, if the outline of imprint 1310 is substantially jagged, this may indicate that one or more of the LEDs in LED unit are misaligned or that there are one or more redundant LEDs. In addition, UV sensitive paper 1308 can be examined for additional imprints outside of the imprint 1310 corresponding to the pre-curing area. For example, if an imprint exists in the interior regions of UV sensitive paper 1308, this may indicate that UV light is being scattered due to misalignment of the LEDs. The location of the additional imprints or jagged features on UV sensitive paper 1308 can indicate the position of the one or more LEDs that need repositioning. If it is determined that one or more LEDs should be repositioned or removed, the adjustment can be made and another test procedure can be conducted until an acceptable imprint 1310 is produced on UV sensitive paper 1308. If imprint 1310 is suitably shaped and sized to provide pre-cured LOCA during a pre-curing process that is substantially defect free, LED unit and mask assembly can be used for a subsequent pre-curing process.

Figure 14:
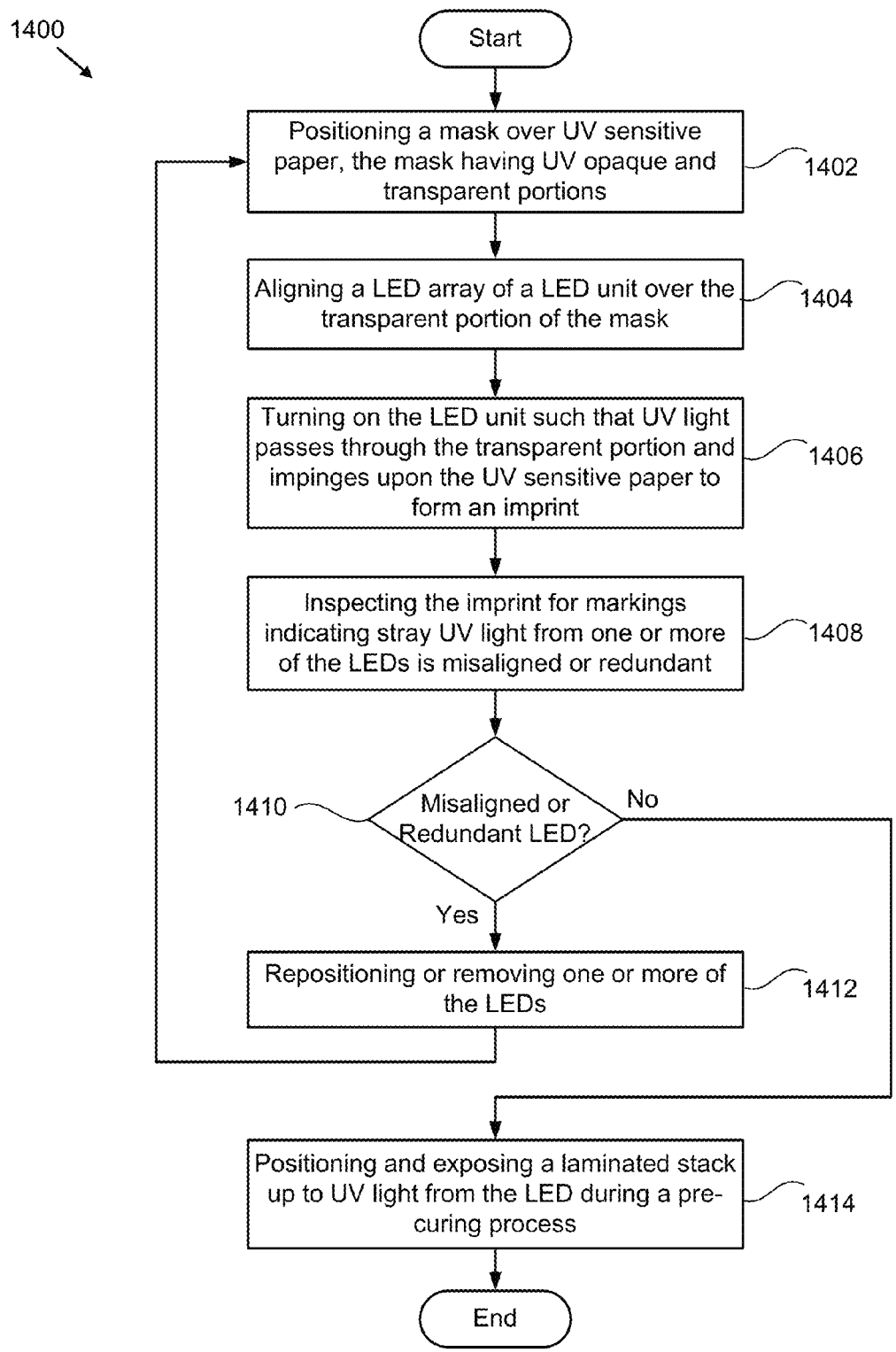
FIG. 14 shows a flowchart showing steps involved for testing a LED unit assembly for exposing a laminated stack up to UV light during a pre-curing process.

FIG. 14 shows a flowchart 1400 showing steps involved for testing a LED unit assembly for exposing a laminated stack up to UV light during a pre-curing process. The laminated stack up includes a LOCA between a first substrate and a second substrate, such as cover glass 202 and sensor layer 208 of laminated stack up 200 of FIG. 2A. At 1402, the mask is positioned over UV sensitive paper. The mask can have an opaque portion and a transparent portion, the opaque portion configured to block UV light from passing through and the transparent portion configured to allow UV light to pass through. The transparent portion can have a shape and size corresponding to a pre-curing area of the laminated stack up. In some embodiments, the mask is rectangular in shape with interior and exterior opaque portions and a transparent portion positioned between the interior and exterior opaque portions, such as mask 1102 of FIG. 11. At 1404, the LED array of an LED unit is aligned over the mask. The LED unit can have a number of UV light emitting LEDs where the LEDs are arranged in an array that has a shape and size corresponding to the shape and size of the transparent portion of the mask. For example, LED unit 1200 of FIG. 12 includes an LED array 1208 that can be shaped and sized to corresponding to the shape and size of transparent portion 1106 of mask 1102 of FIG. 11. At 1406, the LED unit is turned on so that UV light can pass through the transparent portion of the mask and impinge upon to form an imprint on the UV sensitive paper. At 1408, the imprint on the UV sensitive paper is inspected for markings that can indicate stray UV light caused by light hitting, for example, surfaces of the mask. In some cases, this can indicate that one or more of the LEDs are misaligned. In other cases, the markings can indicate redundant or extraneous LEDs. At 1410, if it is determined that one or more LEDs are misaligned or redundant, at 1412 the misaligned LEDs are repositioned and the redundant LEDs are removed. Then the positioning, aligning, turning on the LED unit and inspecting an imprint on subsequent UV sensitive paper(s) is repeated until it is determined that the LEDs are suitably aligned and non-redundant. That is, there are substantially no markings on the UV sensitive papers indicating stray UV light. At 1414, the laminated stack up can be positioned below the mask during a pre-curing process to expose the LOCA in the laminated stack up to UV light in the pre-curing area. The result should be substantially no visible defects existing in the LOCA and the laminated stack up after the pre-curing process.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium for controlling manufacturing operations or as computer readable code on a computer readable medium for controlling a manufacturing line. The computer readable medium is any data storage device that can store data which can thereafter be read by a computer system. Examples of the computer readable medium include read-only memory, random-access memory, CD-ROMs, HDDs, DVDs, magnetic tape, and optical data storage devices. The computer readable medium can also be distributed over network-coupled computer systems so that the computer readable code is stored and executed in a distributed fashion.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A method for curing a laminated stack up comprising a layer of uncured liquid optically clear adhesive (LOCA) disposed between a first substrate and a second substrate, the layer of LOCA having an edge portion that defines a perimeter of the layer of LOCA and a central portion that does not include the edge portion, the method comprising:
   performing a pre-curing operation using a movable shutter, comprising:
      exposing the edge portion of the layer of LOCA to ultraviolet (UV) light such that the edge portion is at least partially solidified and such that LOCA material from the layer of LOCA is prevented from flowing beyond the perimeter of the LOCA layer, wherein the movable shutter defines a blocked area that blocks the central portion from exposure to UV light, and
      exposing the edge portion and a first part of the central portion of the layer of LOCA to UV light such that the edge portion and the first part of the central portion is at least partially cured, wherein the blocked area of the movable shutter is reduced such that the movable shutter blocks a remainder part of the central portion without blocking the first part of the central portion and the edge portion from UV light; and
   performing a curing operation, comprising:
      exposing substantially the entire layer of LOCA to UV light such that substantially the entire layer of LOCA is fully cured, wherein a transition between the edge portion and the first part of the central portion and a transition between the first part and the remainder part of the central portion are substantially imperceptible as viewed from a top surface of the laminated stack up.

2. The method of claim 1, wherein the movable shutter forms a rectangular shaped blocked area, wherein reducing the blocked area includes reducing a perimeter of the blocked area.

3. The method of claim 2, wherein corners of the rectangular shaped block area are each moved an equal distance with respect to a center of the rectangular shaped block area.

4. The method of claim 1, wherein the central portion of the layer of LOCA includes multiple parts that are exposed to different amounts of UV light.

5. The method of claim 4, wherein after performing the curing operation, transitions between the multiple parts of the central portion are substantially imperceptible as viewed from a top surface of the laminated stack up.

6. The method of claim 1, wherein during the pre-curing operation the edge portion and the first part of the central portion do not become fully cured.

7. The method of claim 6, wherein more of the edge portion is cured during the pre-curing operation than the first part of the central portion.

8. The method of claim 1, wherein the performing a pre-curing operation results in a partially cured gradient across the edge portion and the first part of the central portion.

9. The method of claim 8, wherein the partially cured gradient is gradual.

10. The method of claim 1, further comprising:
    testing pre-curing components for properly aligned UV light exposure prior to the performing a pre-curing operation.

11. The method of claim 10, further comprising:
    repositioning one or more pre-curing components when the testing indicates improper alignment thereof.

12. The method of claim 1, wherein during the pre-curing and curing operations the UV light is shone on the laminated stack up at a substantially perpendicular orientation with respect to the top surface of the laminated stack up.

13. The method of claim 1, wherein the laminated stack up is part of a display assembly and the edge portion is proximate to an electrical contact of the display assembly, wherein exposing the edge portion of the layer of LOCA prevents the LOCA material from contacting the electrical contact.

14. The method of claim 1, the performing a pre-curing operation further comprising:
    exposing the edge portion, the first part of the central portion, and a second part of the central portion of the layer of LOCA to UV light such that the edge portion, the first part of the central portion, and the second part of the central portion are all at least partially cured, wherein the blocked area of the movable shutter is further reduced such that the movable shutter blocks a second remainder part of the central portion without blocking the second part of the central portion, the first part of the central portion, and the edge portion from UV light.

15. The method of claim 1, wherein the movable shutter is part of a movable mask.

16. The method of claim 1, wherein the performing a pre-curing operation includes using multiple movable shutters.

17. The method of claim 1, wherein the performing a pre-curing operation includes locating the movable shutter between the UV light and the layer of LOCA.

18. The method of claim 1, wherein the cured layer of LOCA bonds components together for a portable electronic device.

19. The method of claim 1, wherein the performing a pre-curing operation and the performing a curing operation use UV light of differing intensities.

* * * * *